United States Patent [19]

Hammar

[11] 3,949,091

[45] Apr. 6, 1976

[54] 8-SUBSTITUTED DIBENZOBICYCLO[3.2.1]OCTADIENES FOR TREATING DEPRESSION

[75] Inventor: Walton James Hammar, St. Paul, Minn.

[73] Assignee: Riker Laboratories, Inc., Northridge, Calif.

[22] Filed: Dec. 9, 1974

[21] Appl. No.: 530,669

Related U.S. Application Data

[62] Division of Ser. No. 194,056, Oct. 29, 1971, Pat. No. 3,860,652.

[52] U.S. Cl. .............................................. 424/330
[51] Int. Cl.² ......................................... A61K 3/135
[58] Field of Search ................................... 424/330

[56] References Cited
UNITED STATES PATENTS

| | | | |
|---|---|---|---|
| 3,422,104 | 1/1969 | Schroter et al. | 260/570.8 |
| 3,423,425 | 1/1969 | Wilhelm | 260/570.8 |
| 3,452,102 | 6/1969 | Lednicco | 260/570.9 |

FOREIGN PATENTS OR APPLICATIONS

| | | | |
|---|---|---|---|
| 1,953,334 | 4/1971 | Germany | 260/570.9 |

*Primary Examiner*—Stanley J. Friedman
*Attorney, Agent, or Firm*—Alexander, Sell, Steldt & DeLaHunt

[57] ABSTRACT

Dibenzobicyclo[3.2.1]octadienes substituted in the 8 position by substituted aminoalkyl groups, and salts thereof, are described. These compounds have central nervous system activity as anti-depressants.

5 Claims, No Drawings

8-SUBSTITUTED DIBENZOBICYCLO[3.2.1]OCTADIENES FOR TREATING DEPRESSION

This is a division of application Ser. No. 194,056 filed Oct. 29, 1971, now U.S. Pat. No. 3,860,652.

BACKGROUND OF THE INVENTION

This invention involves the field of CNS-active substances and more particularly is directed to substituted dibenzobicyclo[3.2.1]octadienes.

Many dibenzocycloalkane and dibenzocycloalkene systems are known, and some of these have physiological activity. It has become apparent in recent years that minor structural variations on a given system of organic compounds can have important and unpredictable effects on physiological activity. It is believed that the physiological activity of the novel aminoalkyldibenzobicyclooctadienes of the present invention is quite unexpected.

Prior publications showing dibenzocycloalkane and -alkene systems include the following: U.S. Pat. Nos. 3,258,488; 3,275,689; 3,332,977; 3,337,623 and 3,234,279.

Prior publications showing dibenzobicyclo[3.2.1]octadienes include: Cristol et al, J. Am. Chem. Soc. 87, 2870 (1965); Cristol et al, J. Org. Chem. 30, 1956 (1965); Kitahonoki et al, Tetrahedron 24, 4605 (1968) and additional publications by Cristol et al and others.

The present invention provides certain novel 8-substituted dibenzobicyclo[3.2.1]octadiene compounds with advantageous central nervous system activity. The substituent at the 8 position must be a substituted aminoalkyl group. These compounds are anti-depressants with a relatively low degree of side effects. In particular, they have no significant effect on heart rate and blood pressure at doses which produce effects associated with anti-depressant activity in test animals. Other effects on the central nervous system, such as anorexia, are also observed.

DETAILED DESCRIPTION OF THE INVENTION

This invention relates to compounds of the formula

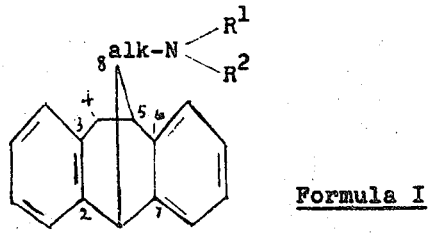

Formula I wherein $R^1$ is hydrogen or lower alkyl, $R^2$ is lower alkyl and —alk— is methylene, ethylene or methylmethylene, and acid addition salts thereof. Lower alkyl as used herein means alkyl radicals having 1 to 4 carbon atoms. The compounds of the invention and their pharmaceutically acceptable acid addition salts are active on the mammalian central nervous system. In particular, they show the phamacological profile of anti-depressant agents.

The acid addition salts of the compounds of the present invention with inorganic or organic (carboxylic) acids are useful per se, when said salts are pharmaceutically acceptable, or the salts are useful as intermediates from which the free base compounds may be produced, or the salts may be used as intermediates to prepare other salts.

Acid addition salts of the compounds of the present invention can be prepared by reaction of acids with the free base of Formula I. For example, reaction of the free base with stoichiometrically equivalent amounts of acids such as hydrohalic acids, for example, hydrochloric acid, hydrobromic acid and the like; sulfuric acid, phosphoric acid, etc.; or with organic acids such as oxalic acid, acetic acid, lactic acid, tartaric acid, citric acid and the like, provides acid addition salts in relatively pure form. Non-pharmaceutically acceptable acid addition salts can be converted into pharmaceutically acceptable addition salts either by neutralization followed by reaction with a suitable pharmaceutically acceptable acid or by an ion exchange reaction.

The group -alk- is preferably methylene, the group $R^1$ is preferably methyl, ethyl or hydrogen and the group $R^2$ is preferably methyl or ethyl. Most preferred compounds of the invention are salts of the compounds 8-(N-methylaminomethyl)dibenzobicyclo-[3.2.1]octadiene and 8-(N,N-dimethylaminomethyl)dibenzobicyclo-[3.2.1]octadiene. The most preferred salt is presently the hydrochloride salt, which is a pharmaceutically acceptable salt.

The compounds of the invention have been found to demonstrate anti-depressant activity when evaluated in two rodent test methods commonly used for the detection of such activity. These two tests measure antagonism of the depressant syndrome produced following administration of reserpine or of Ro 4-1284 (2-hydroxy-2-ethyl-3-isobutyl-9,10-dimethoxy-1,2,3,4,6,7-hexahydrobenzo(a)-quinolizine). These test methods are described by Sulzer et al, Ann. N.Y. Acad. Sci. 96:279 (1962). It has been found that the preferred compounds of the invention, for example anti-8-(N-methylaminomethyl)dibenzobicyclo[3.2.1]-octadiene and its salts, demonstrate activity in mice and rats at dose levels the same as those of active doses of imipramine hydrochloride, a well-known anti-depressant agent, on a milligram per kilogram body weight basis. This information serves to estimate an effective oral human therapeutic dose of 25 to 100 mg/day, although doses as small as 10 mg/day or as large as 200 mg/day could be suitable in unusual instances. The preferred compounds of the invention have a therapeutic index greater than 5. The compounds of the invention may also be administered orally or parenterally.

The compounds of Formula I can be used as medicaments in the form of pharmaceutical preparations. Thus these compounds or their salts can, for example, be formulated in admixture with suitable known organic or inorganic inert pharmaceutical carrier materials. Then may be administered orally in the form of tablets, powders, sustained release pellets and the like, or they may be administered orally or parenterally in the form of aqueous solutions or suspensions. Such dosage forms are readily prepared by conventional methods.

The anti-depressant action of the compounds of the present invention is sufficiently extended in duration so that protection from depressed states is obtained for periods of about three hours or more by a single nontoxic dose in animals.

Broadly speaking the compounds of the invention can be prepared by a process which comprises forming a Grignard reagent from the known compound 8-chlorodibenzobicyclo[3.2.1]-octadiene, converting the Grignard reagent to 8-(hydroxyalkyl)-substituted dibenzobicyclo[3.2.1]octadiene, and treating the latter compound to replace the hydroxyl group with a primary or secondary amine residue having the formula

wherein $R^1$ is hydrogen or lower alkyl and $R^2$ is lower alkyl.

The following series of equations illustrates the steps in several reaction sequences which can be employed in producing the compounds of the invention according to the broad process described. In these equations $R^1$ and $R^2$ have the significance set forth above, and Q is methyl or p-tolyl.

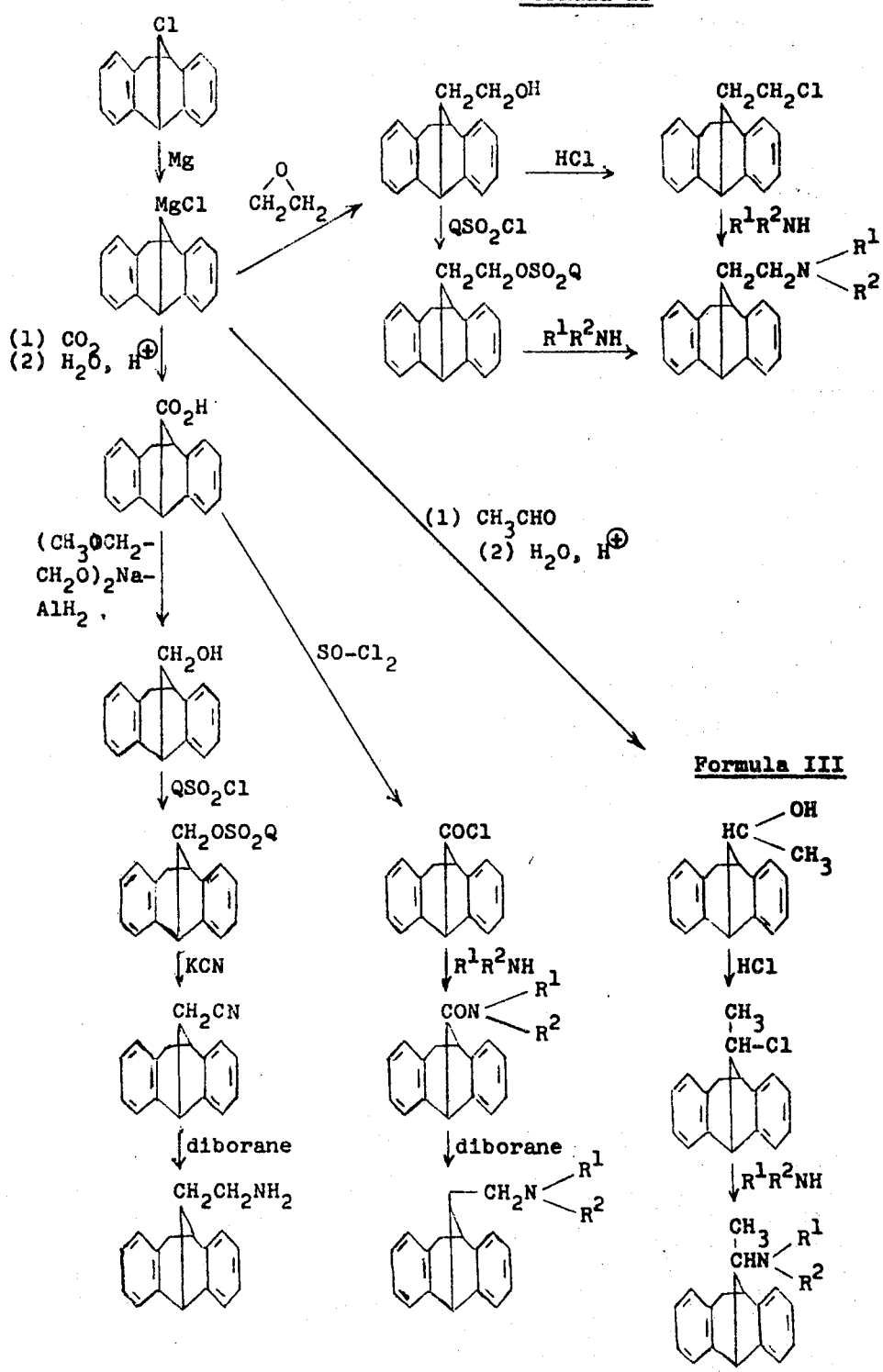

It is important to observe that the 8 position is a non-symmetrical position, and therefore geometrical as well as optical isomerism will exist in the compounds of the invention. Thus both syn- and anti-geometrical isomers of the compounds of invention exist. The geometrical configuration of the compounds of the present invention has been established by nuclear magnetic resonance spectral measurements and analysis. Both geometrical forms demonstrate biological activity.

The compounds of the invention are conveniently prepared starting with the known compound 8-anti-chlorodibenzobicyclo[3.2.1]octadiene. This compound is converted to the magnesium Grignard reagent by a Grignard reaction. This Grignard reagent may be used to prepare the compounds of the invention by numerous synthetic sequences, for example it may be reacted with carbon dioxide using standard techniques to prepare the corresponding 8-carboxylic acid in the anti form. The syn form of the acid is also formed and is separated by fractional crystallization.

These acids are readily converted to the corresponding acid chlorides or bromides, for example, by reaction with thionyl chloride or bromide, or with phosphorus pentachloride. The acid halide then is reacted with a primary or secondary amine to provide an amide. Such amides are readily reduced, for example, using diborane as the reducing agent, to provide compounds of Formula I wherein —alk— is methylene. These reactions do not change the stereochemistry at the 8 position. Therefore, either the syn or the anti isomer may be synthesized depending on the starting configuration.

The novel carboxylic acids and derivatives thereof which are intermediates in the process are included within the compounds of the invention.

Compounds of the invention wherein —alk— is ethylene and the compounds are in the "anti" stereo form are prepared by reacting the Grignard reagent of 8-anti-chlorodibenzobicyclo-[3.2.1]octadiene with ethylene oxide. The reaction provides the primary alcohol of Formula II.

The primary alcohol II can be converted to the corresponding amine of Formula II by known synthetic sequences such as conversion first to the primary halide by reaction with hydrohalic acid such as hydrochloric acid or hydrobromic acid, followed by reaction with a primary or secondary amine. Alternatively the alcohol may be converted to a methanesulfonic or p-toluenesulfonic ester followed by a displacement reaction with a primary or secondary amine.

In order to obtain compounds of Formula I wherein —alk— is methylmethylene and the stereochemistry is anti, the Grignard reagent described hereinabove is reacted with acetaldehyde to provide the corresponding secondary alcohol of Formula III. This secondary alcohol may be converted to a methanesulfonic or p-toluenesulfonic ester and then to a product compound of Formula I by reaction with a primary or secondary amine.

In order to prepare compounds of the invention wherein —alk— is ethylene and the stereochemistry is syn, an additional and alternative method is desirable, since the compound syn-8-chlorodibenzobicyclo[3.2.1]octadiene is obtained only in low yields by presently known methods. One alternative is to use the syn-8-carboxydibenzobicyclo[3.2.1]octadiene and convert it into the desired intermediates by known synthetic sequences. For example, the carboxyl group can be reduced to a hydroxymethyl group, the hydroxymethyl group converted to a methanesulfonic or p-toluenesulfonic ester, the ester group displaced by cyanide, the cyano group reduced to an amino group and the amino group alkylated to a secondary or tertiary amine of Formula I.

The following non-limiting examples further illustrate the preparation of the novel compounds of the invention, both intermediates and compounds of Formula I. The optical isomers are not separated in the course of the various processes shown and therefore the dl-forms are obtained.

EXAMPLE 1

To a suspension of 3.15 g. (0.130 mole) of magnesium filings in 20 ml. of tetrahydrofuran is added 29.5 g. (0.126 mole) of 8-anti-chlorodibenzobicyclo[3.2.1]octadiene while maintaining the solution at reflux. Five drops of 1,2-dibromomethane are added. The mixture is maintained at reflux temperature for about 16 hours. The mixture is then cooled to $-25°$ C. with a Dry Ice-acetone bath, and carbon dioxide is bubbled in rapidly. The addition of carbon dioxide is continued for 1.5 hours, then the mixture is warmed to room temperature. The mixture is added carefully to an aqueous solution saturated with ammonium chloride. The water layer is separated and extracted with dichloromethane, then extracted twice with diethyl ether, and the organic layers are combined. The organic layers are evaporated under vacuum to a non-volatile residue. Diethyl ether is added, and the solution is washed with 5 percent sodium hydroxide solution twice. The aqueous solution is then acidified, washed with dichloromethane, and dried over magnesium sulfate. The solution is then filtered and evaporated under reduced pressure to provide 8-carboxydibenzobicyclo[3.2.1]octadiene. This solid is fractionally recrystallized from benzene to provide a white solid, melting point $175°-180°$ C. Nuclear magnetic resonance analysis of this isomer shows it to be essentially pure (greater than 95 percent) anti-isomer.

Analysis: Calculated for $C_{17}H_{14}O_2$: C, 81.5; H, 5.64 Found: C, 81.8; H, 5.60.

The mother liquors from the recrystallization of the anti isomer are evaporated to provide a residue which is fractionally recrystallized from benzene or ethanol. The essentially pure syn dl isomer is obtained which has m.p. $218°-222°$ C. Its purity is checked by its nuclear magnetic resonance spectrum.

It should be noted that the amount of syn isomer obtained is substantially decreased by maintaining the temperature of the solution to which carbon dioxide is added at $-15°$ C. until the aqueous ammonium chloride solution is added.

EXAMPLE 2

A solution of 65 ml. of thionyl chloride and 18 g. (0.073 mole) of anti-8-carboxydibenzobicyclo[3.2.1]octadiene is heated to its reflux temperature and maintained at that temperature for one hour. The thionyl chloride is removed by evaporation under reduced pressure. Benzene is added (about 50 ml.), and the mixture is again evaporated to dryness under reduced pressure. Benzene (75 ml.) is added, the flask is fitted with a gas inlet and a Dry Ice-acetone condenser, and the mixture is cooled to 0° C. Methylamine is added through the gas inlet, and the solution is allowed to warm gradually to room temperature. After adding an excess of methylamine, the mixture is stirred overnight at room temperature. Diethyl ether is added, then water; the organic layer is separated off and then washed with 2 N HCl and 5 percent sodium hydroxide solution, and finally with a saturated sodium chloride solution. The organic layer is dried over magnesium sulfate, filtered, then evaporated under reduced pressure to give the desired product. The residual white solid is recrystallized from ethanol to give anti-8-(N-methylcarbox-amido)dibenzobicyclo[3.2.1]octadiene, m.p. 230°–233° C.

Analysis: Calculated for $C_{18}H_{17}NO$: C, 82.3; H, 6.5; N, 5.3 Found: C, 82.1; H, 6.6; N, 5.3.

EXAMPLE 3

Using the procedure of Example 2, syn-8-carboxydibenzobicyclo[3.2.1]octadiene is converted to syn-8-(N-methyl-carboxamido)dibenzobicyclo[3.2.1]octadiene, m.p. 210°–211° C.

Analysis: Calculated for $C_{18}H_{17}NO$: C, 82.3; H, 6.5; N, 5.3 Found: C, 82.2; H, 6.3; N, 5.2.

EXAMPLE 4

A solution of 25 ml. of thionyl chloride and 7.0 g. (28 mmole) of anti-8-carboxydibenzobicyclo[3.2.1]octadiene is heated to its reflux temperature and maintained at that temperature on a steam bath for one hour. The thionyl chloride is removed by evaporation under reduced pressure. A solution of 6.8 g. (150 mmole) of dimethylamine in 25 ml. of benzene is added carefully with cooling, and the mixture is then poured into about 60 ml. of 2 N hydrochloric acid solution, and about 100 ml. each of benzene and diethyl ether are added. The layers are separated, and the organic layer is washed with saturated sodium chloride solution, then dried over anhydrous magnesium sulfate. The solution is filtered, then evaporated under reduced pressure to provide solid anti-8-(N,N-dimethylcarboxamido)-dibenzobicyclo[3.2.1]octadiene, m.p. 128° C. (d.) after recrystallization from ethanol.

Analysis: Calculated for $C_{19}H_{19}NO$: C, 82.5; H, 6.9; N, 5.1 Found: C, 82.5; H, 7.0; N, 5.1.

EXAMPLE 5

Using the procedure of Example 4, syn-8-carboxydibenzobicyclo[3.2.1]octadiene is converted to syn-8-(N,N-dimethylcarboxamido)dibenzobicyclo[3.2.1]octadiene.

EXAMPLE 6

Anti-8-(N,N-dimethylcarboxyamido)dibenzobicyclo[3.2.1]-octadiene (4.7 g., 17 mmole) is suspended in 35 ml. of tetrahydrofuran, and a solution of 1 molar borane in 35 ml. of tetrahydrofuran is added while maintaining the temperature of the reaction at 0° C. The mixture is stirred for 30 minutes, then heated to reflux temperature and maintained at this temperature overnight. The mixture is cooled using an ice bath, and 5 ml. of water are added dropwise very carefully, and the mixture is then stirred for 30 minutes. Next 17 ml. of 6 N HCl are added, and the mixture is heated to its reflux temperature and maintained at this temperature for one hour. The mixture is evaporated under reduced pressure to remove the tetrahydrofuran. To the residue is added 100 ml. each of benzene and diethyl ether and about 50 ml. of water. The layers are separated, the organic layer is extracted with 25 ml. of 3 N HCl, and the acid layers are combined. The acid layers are made basic with dilute sodium hydroxide. The product is extracted into several portions of benzene, which are combined and dried over anhydrous magnesium sulfate. The solution is filtered, then evaporated under reduced pressure. The residue is dissolved in isopropanol and hydrochloric acid is added. The white solid isolated by filtration is recrystallized to provide anti-8-(N,N-dimethylaminomethyl)di-benzobicyclo[3.2.1]octadiene hydrochloride, m.p. 263°–265° C. (d.)

Analysis: Calculated for $C_{19}H_{21}N \cdot HCl$: C, 76.1; H, 7.4; N, 4.7 Found: C, 76.0; H, 7.3; N, 4.6.

EXAMPLE 7

Using the procedure of Example 6, syn-8-(N,N-dimethyl-carboxamido)dibenzobicyclo[3.2.1]octadiene is reduced to provide syn-8-(N,N-dimethylaminomethyl)dibenzobicyclo[3.2.1]octadiene hydrochloride, m.p. 247°–249° C.

Analysis: Calculated for $C_{19}H_{21}N \cdot HCl$: C, 76.1; H, 7.4; N, 4.7 Found: C, 75.9; H, 7.4; N, 4.6.

EXAMPLE 8

Anti-8-(N-methylcarboxamido)dibenzobicyclo[3.2.1]octadiene (16 g., 61 mmole) is dissolved in 120 ml. of tetrahydrofuran and cooled to 0° C. The mixture is stirred while adding a 1 molar solution of borane in 120 ml. of tetrahydrofuran. The mixture is warmed slowly to room temperature and finally heated to reflux temperature and maintained at this temperature overnight. The mixture is cooled to 0° C., 10 ml. of water are added, the mixture is stirred for 15 minutes, then the mixture is heated to its reflux temperature for 1.5 hours. The mixture is cooled, the solvent is removed by evaporation under vacuum, then diethyl ether is added. The acidic aqueous phase is separated and made basic with dilute sodium hydroxide solution. The solution is then extracted with dichloromethane and the organic layers are combined and dried over anhydrous magnesium sulfate. The organic layers are filtered and evaporated under vacuum. The residue is dissolved in 50 ml. of isopropanol and added to a solution of 2.4 gm. of hydrochloric acid in 100 ml. of isopropanol. After isolation the anti-8-(N-methylaminomethyl)dibenzobicyclo[3.2.1]-octadiene hydrochloride is recrystallized from isopropanol. The recrystallized material has the melting point 231°–232° C.

Analysis: Calculated for $C_{18}H_{19}N \cdot HCl$: C, 75.7; H, 7.0; N, 4.9 Found: C, 75.4; H, 7.0; N, 4.7.

EXAMPLE 9

Using the procedure of Example 8, syn-8-(N-methylcarboxamido)dibenzobicyclo[3.2.1]octadiene is reduced to provide syn-8-(N-methylaminomethyl)dibenzobicyclo[3.2.1]octadiene hydrochloride, m.p.

263°–264° C.

Analysis: Calculated for $C_{18}H_{19}N\cdot HCl$: C, 75.7; H, 7.0; N, 4.9. Found: C, 75.6; H, 7.1; N, 4.9.

EXAMPLE 10

Syn-8-carboxydibenzobicyclo[3.2.1]octadiene (7.3 g., 29 mmole) in 60 ml. of benzene is treated dropwise with a solution of 17 ml. of $(CH_3OCH_2CH_2O)_2NaAlH_2$ (70 percent in benzene, 120 mmole), while maintaining the temperature below 30° C. The mixture is then heated to reflux temperature and refluxed overnight. After cooling, 10 ml. of water are added carefully, then 40 ml. of benzene. The mixture is washed with water, then saturated sodium chloride solution, then the organic layer is dried over magnesium sulfate, filtered and evaporated in vacuo. The solid residue is recrystallized from a benzene-hexane mixture, to give syn-8-hydroxymethyldibenzobicyclo[3.2.1]octadiene, m.p. 92°–95° C.

Analysis: Calculated for $C_{17}H_{16}O$: C, 86.4; H, 6.8 Found: C, 86.0; H, 6.7.

EXAMPLE 11

Syn-8-hydroxymethyldibenzobicyclo[3.2.1]octadiene (5.0 g., 21 mmole) is dissolved in 30 ml. of dichloromethane, flushed with nitrogen, and 3 g. of triethylamine is added. The mixture is cooled to 0° C., and 3.4 g. (30 mmole) of methanesulfonyl chloride is added. The mixture is stirred overnight, then allowed to warm to about 25° C. and stirred for two days. Water is added, and the layers are separated. The organic layer is dried over sodium sulfate, filtered and evaporated in vacuo. The structure of the product, syn-8-(methylsulfonoxymethyl)dibenzobicyclo[3.2.1]octadiene, is confirmed by its infrared spectrum.

EXAMPLE 12

Syn-8-(methylsulfonoxymethyl)dibenzobicyclo[3.2.1]octadiene (7.2 g., 23 mmole) is dissolved in a mixture of 35 ml. of dimethylsulfoxide and 2 g. of potassium cyanide and heated at 75° C. for about 18 hours. The mixture is evaporated in vacuo, the residue is treated with about 100 ml. each of diethyl ether and water, and the organic layer is separated, washed with saturated sodium chloride solution and dried over anhydrous magnesium sulfate. The solution is filtered and evaporated under reduced pressure to a residue which solidifies. The structure of the product is confirmed to be syn-8-(cyanomethyl)dibenzobicyclo[3.2.1]octadiene by its infrared spectrum.

EXAMPLE 13

Syn-8-(cyanomethyl)dibenzobicyclo[3.2.1]octadiene (4.4 g., 18 mmoles) is dissolved in tetrahydrofuran. The mixture is cooled to 0° C. and 25 ml. of 1 N borane solution are added dropwise. The mixture is heated gradually to its reflux temperature and maintained at reflux for about 18 hours, then cooled to 25° C., and 15 ml. of water are added dropwise. Hydrochloric acid (6 N, 20 ml.) is added, and the solution is heated at reflux for 3 hours, then cooled to 25° C. The solution is evaporated to dryness in vacuo, then about 100 ml. of diethyl ether are added, and the solution is made basic with 5 percent sodium hydroxide solution. The organic layer is separated off and extracted with 3 N hydrochloric acid. The acid extract is separated, made basic with sodium hydroxide, then extracted with several portions of dichloromethane. The combined organic extracts are dried over anhydrous sodium sulfate. The mixture is filtered, and the filtrate is evaporated to dryness under vacuum. The structure of the resulting product, syn-8-(2-aminoethyl)dibenzobicyclo[3.2.1]-octadiene, is confirmed by its infrared spectrum.

EXAMPLE 14

Syn-8-(2-aminoethyl)dibenzobicyclo[3.2.1]octadiene (4.5 g., 18 mmole), 11.4 g. of formaldehyde (38 percent aqueous solution) and 13.5 g. of formic acid (97 percent aqueous solution) are mixed and heated on a steam bath for about 18 hours. Concentrated hydrochloric acid (4 ml.) is added, and heating is continued for four hours. The mixture is cooled to about 25° C., and 10 percent aqueous sodium hydroxide is added until the mixture is basic. The mixture is extracted with dichloromethane twice; the organic extracts are combined, washed with saturated sodium chloride solution and dried over sodium sulfate. The mixture is filtered, evaporated under vacuum, and ethyl acetate is added. The organic solution is extracted with aqueous hydrochloric acid, the aqueous layer is separated and made basic with 10 percent sodium hydroxide solution. The basic aqueous solution is extracted with several portions of dichloromethane, the combined extracts are dried over anhydrous sodium sulfate, filtered, and evaporated to dryness under vacuum. The residue is taken up in a few ml. of dichloromethane and purified by column chromatography on neutral alumina, eluting with dichloromethane. The product, syn-8-[2-(N,N-dimethylamino)ethyl]dibenzobicyclo-[3.2.1]octadiene, is converted to its hydrochloride salt in di-ethyl ether by adding hydrochloric acid to a slight excess and collecting the white precipitate. The product is syn-8-[2-(N,N-dimethylamino)ethyl]dibenzobicyclo[3.2.1]octadiene hydrochloride, m.p. 270°–272° C.

Analysis: Calculated for $C_{20}H_{23}N\cdot HCl$: C, 76.4; H, 7.7; N, 4.5 Found: C, 75.7; H, 7.6; N, 4.3.

EXAMPLE 15

Anti-8-(N-methylaminomethyl)dibenzobicyclo[3.2.1]-octadiene is converted to anti-8-(N-acetamido-N-methylamino-methyl)dibenzobicyclo[3.2.1]octadiene by reaction with acetic anhydride in the presence of pyridine, and the product is then reduced to anti-8-(N-ethyl-N-methylaminomethyl)-dibenzobicyclo[3.2.1]octadiene using the method of Example 6.

Anti-8-(N-ethyl-N-methylaminoethyl)dibenzobicyclco[3.2.1]octadiene is isolated as its hydrochloride salt, a white solid, m.p. 208°–210° C.

Analysis: Calculated for $C_{20}H_{23}N\cdot HCl$: C, 76.5; H, 7.6; N, 4.5 Found: C, 76.3; H, 7.7; N, 4.5.

EXAMPLE 16

A mixture of 20 ml. of tetrahydrofuran and 1.7 g. (70 mmole) of magnesium turnings is heated to reflux temperature, and 15 g. (62.5 mmole) of anti-8-chlorodibenzobicyclo[3.2.1]-octadiene in 40 ml. of tetrahydrofuran is added dropwise. Five drops of 1,2-dibromoethane are added to assist in forming the Grignard reagent. After the addition is completed, the reaction mixture is maintained at its reflux temperature for three hours. The mixture is then cooled to 0° C., and a large excess of ethylene oxide is bubbled in over a period of 30 minutes, while maintaining the temperature of the stirred reaction mixture at 0° C. The mixture is warmed to approximately 50° C. for about two hours, then cooled to about 25° C. and poured into about 75 ml. of a saturated ammonium chloride solution.

The organic layer is separated, and the aqueous layer is extracted twice with small portions of diethyl ether. The combined organic layers and ether extracts are dried, then filtered, and the filtrate is evaporated under vacuum to a residue which is an oil. The product is taken up in a few ml. of dichloromethane and separated by column chromatography on alumina. Elution with hexane provides one fraction, dichloromethane provides fractions 2 and 3, and ethyl acetate provides fraction 4. The hexane eluate is discarded. The remaining three are combined, and the solid product is used as isolated for the next process step as described in Example 17. The structure of the product is confirmed by its infrared and nuclear magnetic resonance spectra to be anti-8-(2-hydroxyethyl)dibenzobicyclo[3.2.1]-octadiene.

EXAMPLE 17

Methylsulfonyl chloride (2.3 g., 20 mmole) is added slowly to a solution of 4 g. (16 mmole) of anti-8-(2-hydroxy-ethyl)dibenzobicyclo[3.2.1]octadiene in 15 ml. of pyridine. The mixture is allowed to warm, with stirring, to about 25° C. The mixture is stirred overnight at this temperature. The mixture is then poured into about 75 ml. of cold 6 N hydrochloric acid; the acidic mixture is extracted with several portions of diethyl ether, and the combined ether extracts are washed with cold water. The ether extracts are then dried over anhydrous magnesium sulfate, filtered, and evaporated to dryness under vacuum to obtain the desired product, anti-8-(2-methylsulfonoxyethyl)-dibenzobicyclo[3.2.1]octadiene. The structure of the product is confirmed by infrared spectrum; the product is used as isolated for the next process step as described in Example 18.

EXAMPLE 18

Dimethylamine (6.3 g.) is dissolved in 25 ml. of ethanol. This solution is mixed with 3.5 g. (11 mmole) of anti-8-(2-methanesulfonoxyethyl)dibenzobicyclo[3.2.1]octadiene. The mixture is heated to reflux temperature and maintained at reflux overnight. The reaction mixture is then evaporated to dryness under vacuum, and the residue is dissolved in a benzenediethyl ether mixture. This solution is extracted with 4 N hydrochloric acid. The aqueous layer is separated, made basic with sodium hydroxide, and extracted with several portions of dichloromethane. The organic layer is separated and dried over anhydrous magnesium sulfate. The mixture is filtered and evaporated to dryness under vacuum to yield the desired product, anti-8-[2-(N,N-dimethylamino)ethyl]dibenzobicyclo[3.2.1]octadiene. The product is converted to its hydrochloride salt by reacting it with a slight excess of concentrated hydrochloric acid in isopropanol. The hydrochloride salt precipitates and is isolated by filtration and recrystallized from isopropanol to give a white solid, m.p. 240°–242° C.

Analysis: Calculated for $C_{20}H_{23}N.HCl$: C, 76.4; H, 7.7; N, 4.5 Found: C, 75.9; H, 7.8; N, 4.3.

EXAMPLE 19

Magnesium turnings (2.7 g., 110 mmole) in 15 ml. of tetrahydrofuran are treated with 23.9 g. (100 mmole) of anti-8-chlorodibenzobicyclo[3.2.1]octadiene in 100 ml. of tetrahydrofuran. A small amount of 1,2-dibromoethane is added to assist in the formation of the Grignard reagent. The mixture is heated to its reflux temperature and maintained at reflux overnight. The mixture is then cooled to 0° C., and 6.6 g. (150 mmole) of acetaldehyde in 150 ml. of tetrahydrofuran are added. The mixture is stirred for one hour, and the temperature slowly rises to 15° C. The reaction mixture is poured into about 250 ml. of saturated aqueous amminium chloride, the organic layer is separated, and the aqueous layer is extracted twice with diethyl ether. The organic layer and ether extracts are combined, washed with a saturated aqueous sodium chloride solution, and dried over anhydrous magnesium sulfate. The solution is filtered, then evaporated to dryness under vacuum. The product is isolated from the residue by column chromatography on neutral alumina. The product is placed on the column as a solution in a few ml. of diethyl ether. The column is eluted with hexane, then a benzene-hexane mixture, then with benzene alone, next with diethyl ether, and finally with ethyl acetate. The benzene and ether fractions solidify after evaporation of the solvent to provide the desired product, anti-8-(1-hydroxy-ethyl)dibenzobicyclo[3.2.1]octadiene.

The structure of the product is confirmed by its infrared spectrum.

EXAMPLE 20

A. Anti-8-(1-methylsulfonoxyethyl)dibenzobicyclo[3.2.1]octadiene

The intermediate compound prepared in Example 19, anti-8-(1-hydroxyethyl)dibenzobicyclo[3.2.1]octadiene, is reacted with methanesulfonyl chloride according to the method of Example 11 to provide the methylsulfonoxyethyl-substituted intermediate. The structure is confirmed by its infrared spectrum; the intermediate is used without further purification in the next step of the reaction.

B. Anti-8-[1-(N,N-dimethylamino)ethyl]dibenzobicyclo[3.2.1]-octadiene

The intermediate of part A is reacted with dimethylamine according to the procedure of Example 18. The product is converted to the hydrochloride salt by reaction with a slight excess of hydrochloric acid in isopropanol. The addition of isopropyl ether to the solution promotes the precipitation of the hydrochloride salt. The hydrochloride is recrystallized from a mixture of isopropanol and isopropyl ether. The white solid anti-8-[1-(N,N-dimethylamino)ethyl]dibenzobicyclo[3.2.1]octadiene hydrochloride has m.p. 208°–210° C.

Analysis: Calculated for $C_{20}H_{23}N.HCl$: C, 76.5; H, 7.7; N, 4.5 Found: C, 75.5; H, 7.6; N, 4.4.

What is claimed is:

1. Method of treating depression of the mammalian central nervous system which comprises administering to a mammal a compound of the formula

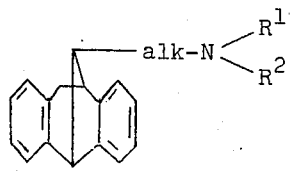

wherein $R^1$ is hydrogen or lower alkyl, $R^2$ is lower alkyl, —alk— is methylene, ethylene or methylmethylene, or an acid addition salt thereof in amount effective to combat depression.

2. Method according to claim 1 wherein the compound is anti-8-(N-methylaminomethyl)dibenzobicyclo[3.2.1]-octadiene hydrochloride.

3. Method according to claim 1 wherein the compound is syn-8-(N-methylaminomethyl)dibenzobicyclo[3.2.1]-octadiene hydrochloride.

4. Method according to claim 1 wherein the compound is anti-8-(N,N-dimethylaminomethyl(dibenzobicyclo[3.2.1]-octadiene hydrochloride.

5. Method according to claim 1 wherein the compound is syn-8-(N,N-dimethylaminomethyl)dibenzobicyclo[3.2.1]-octadiene hydrochloride.

* * * * *